(12) United States Patent
Katchalski et al.

(10) Patent No.: US 9,775,572 B2
(45) Date of Patent: Oct. 3, 2017

(54) RADIATION BEAM INTENSITY PROFILE SHAPER

(71) Applicant: KONINKLIJKE PHILIPS N.V., Eindhoven (NL)

(72) Inventors: Tsvi Katchalski, Binyamina (IL); Ewald Roessl, Henstedt-Ulzberg (DE); Reuven Levinson, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2 days.

(21) Appl. No.: 14/647,568

(22) PCT Filed: Nov. 28, 2013

(86) PCT No.: PCT/IB2013/060479
§ 371 (c)(1),
(2) Date: May 27, 2015

(87) PCT Pub. No.: WO2014/087305
PCT Pub. Date: Jun. 12, 2014

(65) Prior Publication Data
US 2015/0305698 A1 Oct. 29, 2015

Related U.S. Application Data

(60) Provisional application No. 61/733,592, filed on Dec. 5, 2012.

(51) Int. Cl.
*A61B 6/00* (2006.01)
*A61B 6/03* (2006.01)
(Continued)

(52) U.S. Cl.
CPC ............ *A61B 6/4035* (2013.01); *A61B 6/032* (2013.01); *A61B 6/035* (2013.01); *A61B 6/06* (2013.01); *G21K 1/02* (2013.01); *G21K 1/10* (2013.01)

(58) Field of Classification Search
None
See application file for complete search history.

(56) References Cited

U.S. PATENT DOCUMENTS

| 4,581,753 A | * | 4/1986 | Rice | ......................... A61B 6/06 378/146 |
|---|---|---|---|---|
| 7,076,029 B2 | | 7/2006 | Toth et al. | |

(Continued)

FOREIGN PATENT DOCUMENTS

| DE | WO 2008068690 A2 | * | 6/2008 | ............... G21K 1/02 |
|---|---|---|---|---|
| DE | WO 2008068690 A3 | * | 8/2008 | ............... G21K 1/02 |

(Continued)

OTHER PUBLICATIONS

Buzug, T.; Computed Tomography; 2008; Springer; Berlin; p. 497.
Hsieh, J.; Computed Tomography; 2003; SPIE Press; Bellingham, WA.; p. 140.

*Primary Examiner* — Andrew Smyth

(57) ABSTRACT

An imaging system (500) includes a focal spot (510) that rotates along a path around an examination region (506) and emits radiation. A collimator (512) collimates the radiation, producing a radiation beam (516) that traverses a field of view (520) of the examination region and a subject or object therein. A detector array (522), located opposite the radiation source, across the examination region, detects radiation traversing the field of view and produces a signal indicative of the detected radiation. A beam shaper (524), located between the radiation source and the collimator, rotates in coordination with the focal spot and defines an intensity profile of the radiation beam. The beam shaper includes a plurality of elongate x-ray absorbing elements (606) arranged parallel to each other along a transverse direction with respect to a direction of the beam, separated from each other by a plurality of material free regions (604).

21 Claims, 11 Drawing Sheets

(51) Int. Cl.
*A61B 6/06* (2006.01)
*G21K 1/02* (2006.01)
*G21K 1/10* (2006.01)

(56) References Cited

U.S. PATENT DOCUMENTS

| | | | |
|---|---|---|---|
| 9,392,984 B2 * | 7/2016 | Pelc | A61B 6/4035 |
| 2004/0101086 A1 * | 5/2004 | Sabol | A61B 5/4872 378/4 |
| 2004/0101104 A1 * | 5/2004 | Avinash | A61B 6/032 378/98.12 |
| 2005/0089146 A1 * | 4/2005 | Toth | A61B 6/032 378/158 |
| 2005/0163278 A1 * | 7/2005 | Metz | A61B 6/032 378/4 |
| 2006/0052690 A1 * | 3/2006 | Sirohey | A61B 8/481 600/420 |
| 2007/0116181 A1 * | 5/2007 | Arenson | G21K 1/04 378/156 |
| 2007/0140580 A1 * | 6/2007 | Heath | H04N 19/39 382/260 |
| 2008/0036893 A1 * | 2/2008 | De Godzinsky | H04N 3/1562 348/311 |
| 2010/0308229 A1 * | 12/2010 | Bertram | A61B 6/032 250/363.04 |
| 2011/0013742 A1 * | 1/2011 | Zaiki | A61B 6/035 378/15 |
| 2012/0187312 A1 * | 7/2012 | Guez | A44C 5/20 250/492.1 |
| 2013/0182820 A1 | 7/2013 | Proksa | |

FOREIGN PATENT DOCUMENTS

| | | | | |
|---|---|---|---|---|
| DE | 102009012631 A1 * | 9/2010 | | A61B 6/032 |
| JP | 2011110223 A * | 6/2011 | | |
| JP | 2011110223 A | 9/2011 | | |
| WO | 2008068690 A2 | 6/2008 | | |
| WO | 2012042484 A2 | 4/2012 | | |
| WO | 2012077027 A2 | 6/2012 | | |
| WO | 2012174246 A2 | 12/2012 | | |

* cited by examiner

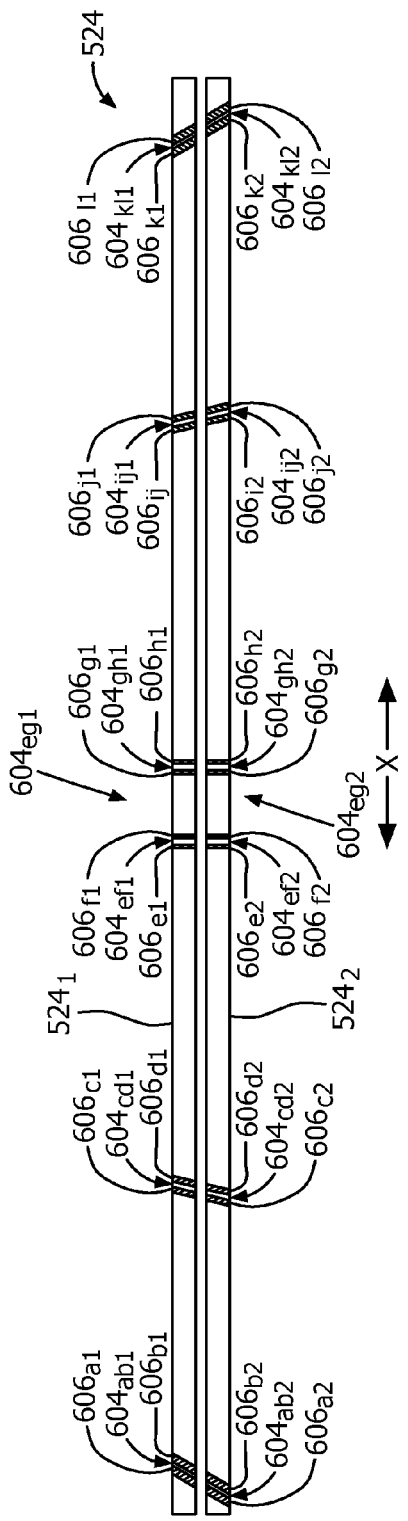
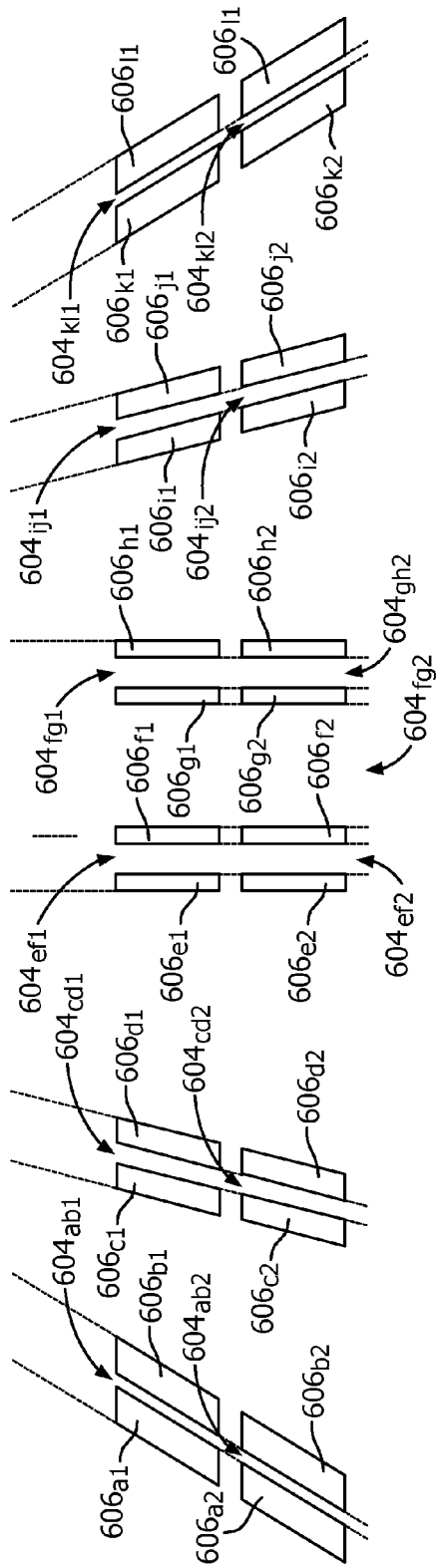
FIG. 9
FIG. 10

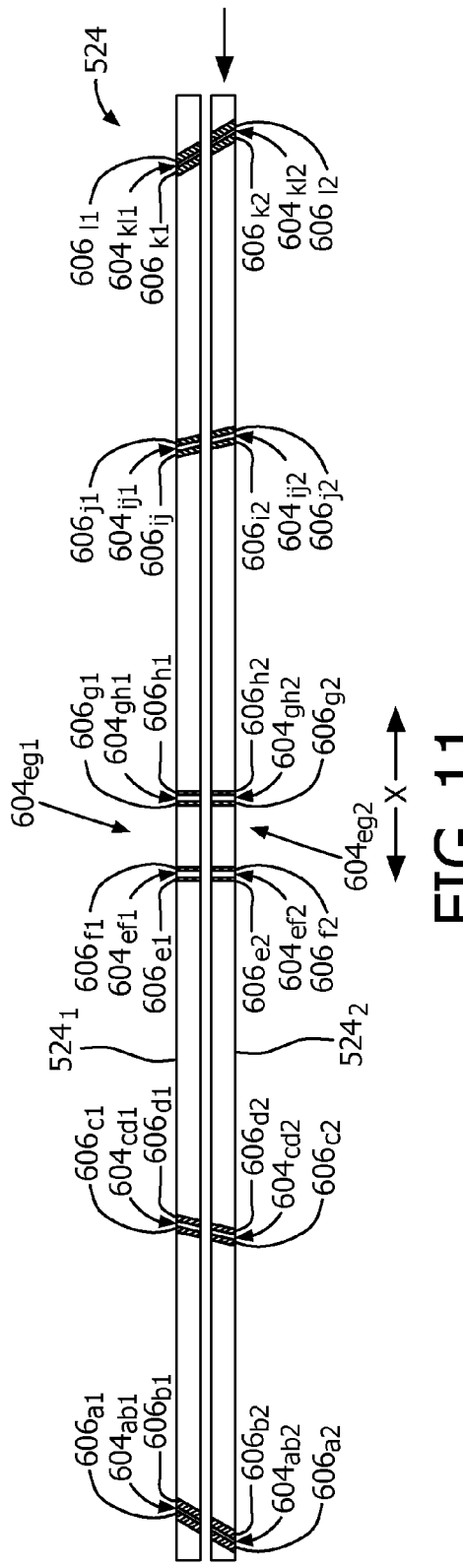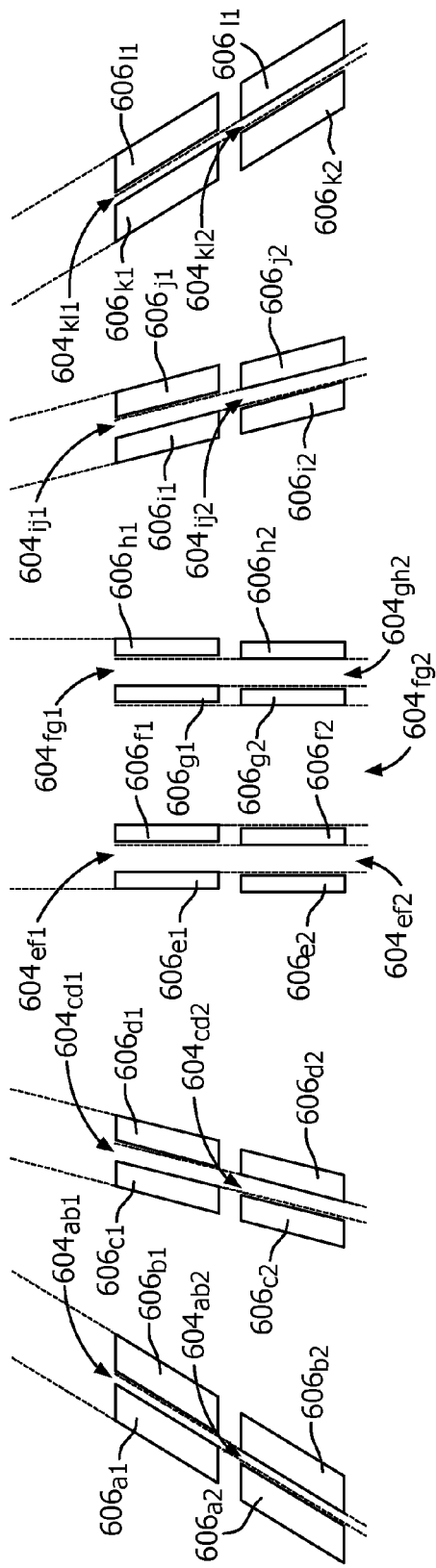
FIG. 11
FIG. 12

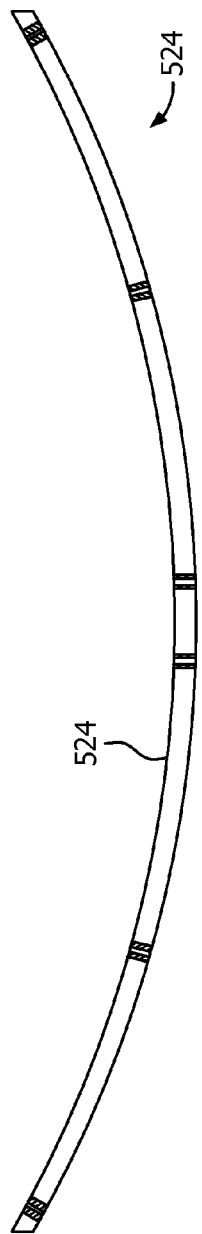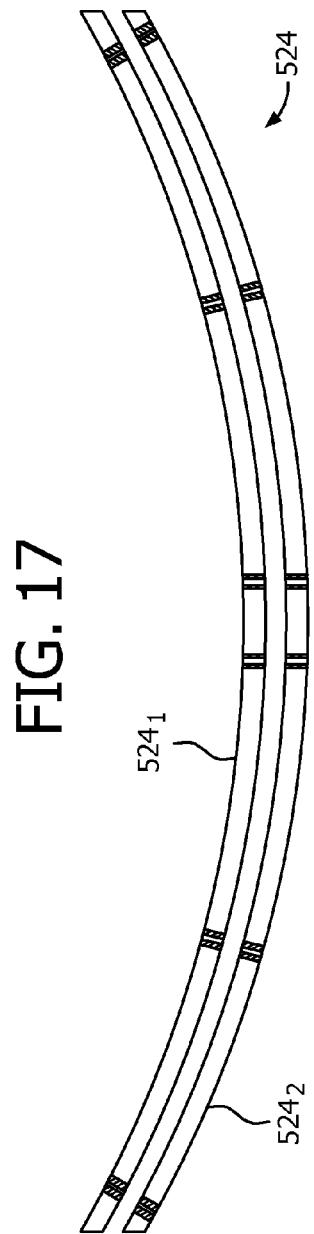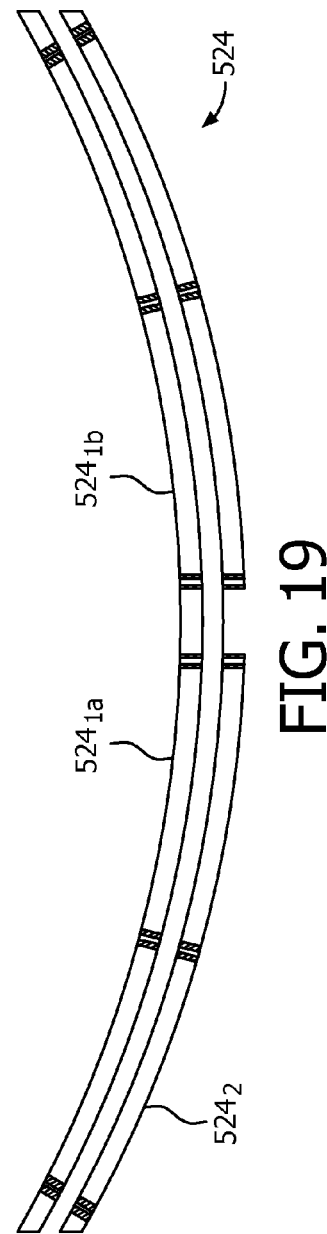

RADIATION BEAM INTENSITY PROFILE SHAPER

CROSS REFERENCE TO RELATED APPLICATIONS

This application is a national filing of PCT application Serial No. PCT/IB2013/060479, filed Nov. 28, 2013, published as WO 2014/087305 A1 on Jun. 12, 2014, which claims the benefit of U.S. provisional application Ser. No. 61/733,592 filed Dec. 5, 2012, which is incorporated herein by reference.

The following generally relates to shaping a radiation beam intensity profile and is described with particular application to computed tomography (CT); however, the following is also amenable to other imaging modalities such as x-ray.

A CT scanner generally includes an x-ray tube that emits radiation from a focal spot in a direction of an examination region. A source collimator is disposed between the focal spot and the examination region and collimates the emitted radiation to produce a beam having a pre-determined geometrical shape. The collimated beam traverses the examination region and a portion of an object or subject therein (which attenuates the beam as a function of the radiodensity of the object or subject) and illuminates a detector array disposed across the examination region, opposite the x-ray tube. The detector produces a signal indicative of the detected radiation. The signal is reconstructed to generate volumetric image data indicative of the portion of the object or subject.

A pre-patient radiation filter (often referred to as a wedge or bowtie filter, due to its physical shape) has been positioned between the focal spot and the source collimator to spatially attenuate the emitted radiation to shape the intensity profile. FIG. 1 schematically illustrates an example of a bowtie filter 102 in connection with a focal spot 104, a source collimator 106, an x-ray beam 108, a detector array 110, an examination region 112, and a portion of a subject or object 114 therein. Due to the physical shape of the bowtie filter 102, portions of the beam 116 that traverse only air traverse thicker portions 118 of the bowtie filter 102, which heavily attenuate the beam, portions of the beam 120 that traverse a central region 121 of the subject traverse thinner portions 122 of the bowtie filter 102, which lightly attenuate the beam, and portions of the beam there between are attenuated based on a smooth transition between the thicker portions 118 and the thinner portion 122.

Unfortunately, such a bowtie filter 102 has limited performance.

For example, the intensity, with an example bowtie filter, at the thicker portions 118 is still about 15%. As such, the bowtie filter 102 may not be well-suited for some photon counting detectors and/or other detectors that suffer from insufficient count rate capabilities. In addition, to achieve the intensity of 15%, the thickness at the thicker portions 118 has to be at least fifty (50) millimeters (mm). For greater modulation, the thickness would need to be larger. However, the size of the bowtie filter 102 defines the minimum spacing needed between the focal spot 104 and the collimator 106, so increasing the size may limit the size of the examination region 112, or, for a given volume between the focal spot 104 and the collimator 106, increasing the size of the bowtie filter 102 may not be an option.

Furthermore, the bowtie filter 102 preferentially attenuates lower energy rays relative to higher energy rays, resulting in beam hardening, thereby changing the x-ray spectrum of the beam exiting the bowtie filter 102, relative to the beam entering the bowtie filter 102. As such, the spectrum of the beam may not be the optimal or desired spectrum. One approach to maintain lower beam hardening is to use a low "Z" (atomic number) material. However, using a low "Z" material reduces dose efficiency. Furthermore, a low "Z" bowtie filter 102 attenuates heavily via the Compton effect, which generates scattered radiation. Scattered radiation produces artifacts in the reconstructed images which degrade image quality and which may require scatter corrections to mitigate. The scattered radiation also contributes to patient dose while not contributing to diagnostic information in the reconstructed images.

Furthermore, the physical profile of every subject is not the same, as some subjects are larger than others, and some subjects are more cylindrical shape whereas others are more elliptical shape. As such, the physical profile of the bowtie filter 102 does not correspond well to a profile of every subject over the entire angular range required for a scan (i.e., at least 180 degrees plus a fan angle). This is shown in FIGS. 2 and 3 where a profile 202 of the bowtie filter 102, relative to the focal spot 104, remains the same as the focal spot 104 rotates from a first angle 204 (FIG. 2) to a second angle 302 (FIG. 3), whereas a profile 206 of the subject 114 changes over the same angular range. As a result, the intensity profile changes as a function of the angular position, resulting in deviations from the desired homogenous illumination, which can degrade image quality.

A similar situation occurs even for more cylindrical shaped subjects where a subject 402 is positioned off-center, shifted from an iso-center 404, as shown in FIG. 4, where the physical profile 202 of the bowtie filter 102 does not correspond to a profile 406 of the off-centered subject 404. In this example, the subject is positioned off-center such that the portion of the beam 408 traversing only air is lightly filtered.

Aspects described herein address the above-referenced problems and others.

In one aspect, an imaging system includes a focal spot that rotates along a path around an examination region and emits radiation. A collimator collimates the radiation, producing a radiation beam that traverses a field of view of the examination region and a subject or object therein. A detector array, located opposite the radiation source, across the examination region, detects radiation traversing the field of view and produces a signal indicative of the detected radiation. A beam shaper, located between the radiation source and the collimator, rotates in coordination with the focal spot and defines an intensity profile of the radiation beam. The beam shaper includes a plurality of elongate x-ray absorbing elements arranged parallel to each other along a transverse direction with respect to a direction of the beam, separated from each other by a plurality of material free regions.

In another aspect, a method includes rotating a focal spot and a beam shaper in coordination on a path around an examination region. The beam shaper includes a plurality of elongate x-ray absorbing elements arranged parallel to each other along a transverse direction with respect to a direction of the beam, separated from each other by a plurality of material free regions, and defines an intensity profile of a radiation beam traversing the examination region. The method further comprising detecting radiation emitted by the focal spot that traverses the beam shaper and the examination region a field of view, and illuminates a detector array located opposite the focal spot, and generating an output signal indicative thereof.

In another aspect, a beam shaper of an imaging system includes a plurality of elongate x-ray absorbing elements arranged parallel to each other along a transverse direction with respect to a direction of the beam, separated from each other by a plurality of material free regions.

In another aspect, a method includes rotating a focal spot and a beam shaper in coordination on a path around an examination region, wherein the beam shaper includes first and second sub-beam shapers, and translating at least one of the first and second sub-beam shapers with respect to the other of the at least first and second sub-beam shapers based on at least one of a patient size, a pre-scan of the patient, a patient position in the examination region, or an anatomy of the patient being scanned, wherein a relative position of the first and second sub-beam shapers with respect to each other defines an intensity profile of a radiation beam traversing the examination region.

The invention may take form in various components and arrangements of components, and in various steps and arrangements of steps. The drawings are only for purposes of illustrating the preferred embodiments and are not to be construed as limiting the invention.

FIG. 1 schematically illustrates an example prior art bowtie filter.

FIG. 2 schematically illustrates the example prior art bowtie filter at a first angle in connection with an elliptical shaped subject.

FIG. 3 schematically illustrates the example prior art bowtie filter at a second angle in connection with the subject.

FIG. 4 schematically illustrates the example prior art bowtie filter in connection with an off centered subject.

FIG. 5 schematically illustrates an example imaging system that includes a beam shaper.

FIG. 6 schematically illustrates a top down view of the example beam shaper.

FIG. 7 schematically illustrates a cross sectional view of a flat single beam shaper.

FIG. 8 schematically illustrates radiation passing through the flat single beam shaper.

FIG. 9 schematically illustrates a cross sectional view of a flat dual beam shaper with aligned sub-beam shapers.

FIG. 10 schematically illustrates radiation passing through the flat dual beam shaper with aligned sub-beam shapers'.

FIG. 11 schematically illustrates a cross sectional view of the flat dual beam shaper with misaligned sub-beam shapers.

FIG. 12 schematically illustrates radiation passing through the flat dual beam shaper with misaligned sub-beam shapers.

FIG. 13 illustrates example flux profiles for the beam shaper of FIGS. 10 and 12.

FIG. 14 schematically illustrates a cross sectional view of flat two (2) sub-beam shapers with one of the sub-beam shapers misaligned.

FIG. 15 schematically illustrates radiation passing through two (2) flat sub-beam shapers.

FIG. 16 illustrates example flux profiles for the beam shaper of FIGS. 14 and 15.

FIG. 17 schematically illustrates a cross sectional view of a curved beam shaper.

FIG. 18 schematically illustrates radiation passing through the dual curved sub-beam shapers.

FIG. 19 schematically illustrates radiation passing through multiple curved beam shapers.

Figure 5:
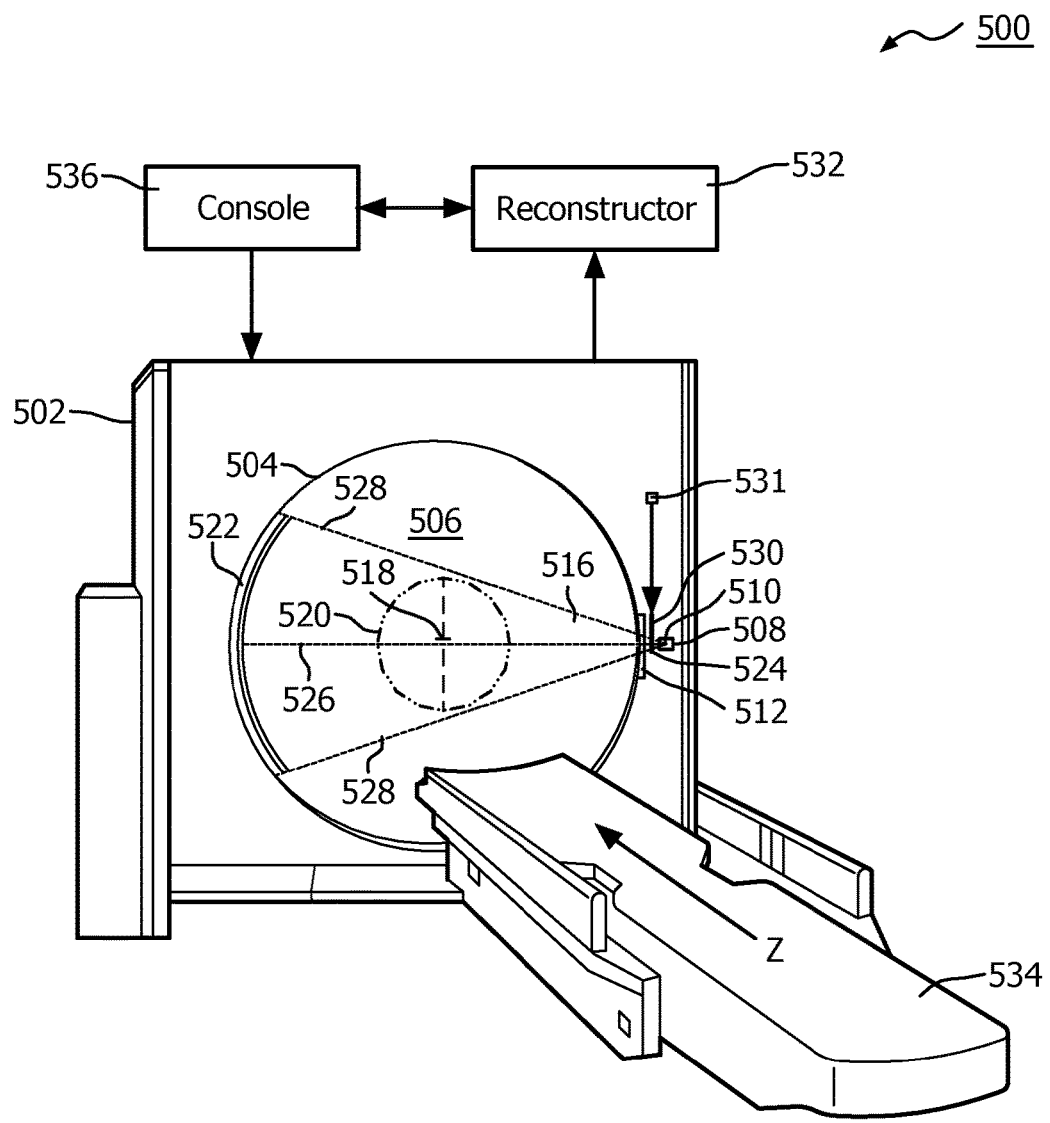

Initially referring to FIG. 5, an imaging system 500 such as a computed tomography (CT) scanner is illustrated. The imaging system 500 includes a stationary gantry 502 and a rotating gantry 504, which is rotatably supported by the stationary gantry 502. The rotating gantry 504 rotates around an examination region 506, about a longitudinal or z-axis.

A radiation source 508, such as an x-ray tube, is supported by the rotating gantry 504 and rotates with the rotating gantry 504 about the examination region 506, and emits radiation, via a focal spot 510, that traverses the examination region 506. A source collimator 512 is disposed between the radiation source 508 and the examination region 506 and includes collimator blades or the like that collimate the emitted radiation to produce a generally fan, cone, or otherwise shaped x-ray beam 516. The illustrated beam 516 is centered about an iso-center 518 of the examination region 506 and defines a generally circular shaped field of view 520.

A radiation sensitive detector array 522 is located opposite the radiation source 508, across the examination region 506. The detector array 522 includes one or more rows of detector pixels. In one instance, the detector pixels are photon counting detector pixels, such as direct conversion photon counting detector pixels, that detect radiation traversing the examination region 506 and generate a signal indicative of the detected radiation. In another instance, the detector pixels are integrating detector pixels and include scintillator/photosensor pairs in which the scintillator converts x-ray photons to light photons which are detected by the photosensor. In yet another instance, the detector pixels includes both direct conversion photon counting detector pixels and scintillator/photosensor based detector pixels.

At least one beam shaper 524 is located between the radiation source 508 (e.g., an x-ray tube housing window) and the collimator 512 in the path of the beam 516 (e.g., in the beam port of an x-ray tube) and shapes a transmission or flux profile of the beam 516 so that beam intensity is greater nearer a central ray 526 of the beam 516 and decreases in a direction away from the central ray 526 and towards outer peripheral rays 528. As described in greater detail below, in one instance, the beam shaper 524 filters the beam 516 such that an intensity of the beam leaving the beam shaper 524 and traversing peripheral regions of the field of view 520 is about 0.00 to 1.00%, such as 0.05%, of the intensity impingent thereon, and an intensity of the beam leaving the beam shaper 524 and traversing a central region of the field of view 520 is about the same as the intensity impingent thereon.

In one instance, such a profile can be achieved while maintaining a small footprint such that the beam shaper 524 can fit in the beam port of the imaging system 500. In addition, the beam shaper 524 includes a material which produces little to no scatter radiation. Furthermore, the beam shaper 524 includes a material which results in little to no beam hardening. In one instance, the at least one beam shaper 524 includes a single beam shaper 524. In another instance, the at least one beam shaper 524 includes a multiple beam shaper 524, such as two, three, etc. beam shapers 524. In such an instance, the multiple beam shapers 524 can be independently or concurrently utilized to dynamically set and/or change the intensity profile while rotating the beam 516 around the examination region 506 and scanning a subject, which allows for changing the intensity profile in coordination with a changing physical profile of a non-cylindrical (e.g., elliptical) shaped subject and/or an off-centered subject.

A support 530 supports the beam shaper 524 in the system 500. In one instance, the support 530 maintains the beam shaper 524 at a static position. In another instance, the support 530 is configured to allow at least one beam shaper 524 to translate along a linear or curved shape (an arc) axis in either or both directions, relative to the focal spot 510, along with rotating the focal spot 510 and beam shaper 524 in coordination on a path around the examination region 506. For this instance, each moveable beam shaper 524 is coupled to a drive system 531, which, in one instance, includes a bearing or the like, which is moved via a motor, under control of a controller, with position sensed by an encoder or the like. Other drive systems 531 are also contemplated herein. Furthermore, each moveable beam shaper 524 may be moved independently and/or concurrently, prior and/or during scanning.

A reconstructor 532 reconstructs the binned data using a spectral and/or conventional reconstruction algorithm and generates spectral and/or conventional volumetric image data indicative of the examination region and the portion of the subject or object therein. Where the shaper 524 is modified during a scan, the decoder information is provided to the reconstructor 532. A subject support 534, such as a couch, supports a subject or object in the examination region 506 and can be used to position the subject or object with respect to x, y, and/or z axes before, during and/or after scanning. A general purpose computing system serves as an operator console 536, and includes an output device such as a display and an input device such as a keyboard, mouse, and/or the like. Software resident on the console 536 allows the operator to control the operation of the system 500, for example, allowing the operator to select a particular beam shaper 524, a motion of the beam shaper 524, etc. directly or indirectly through selecting an imaging protocol, etc.

Figure 6:
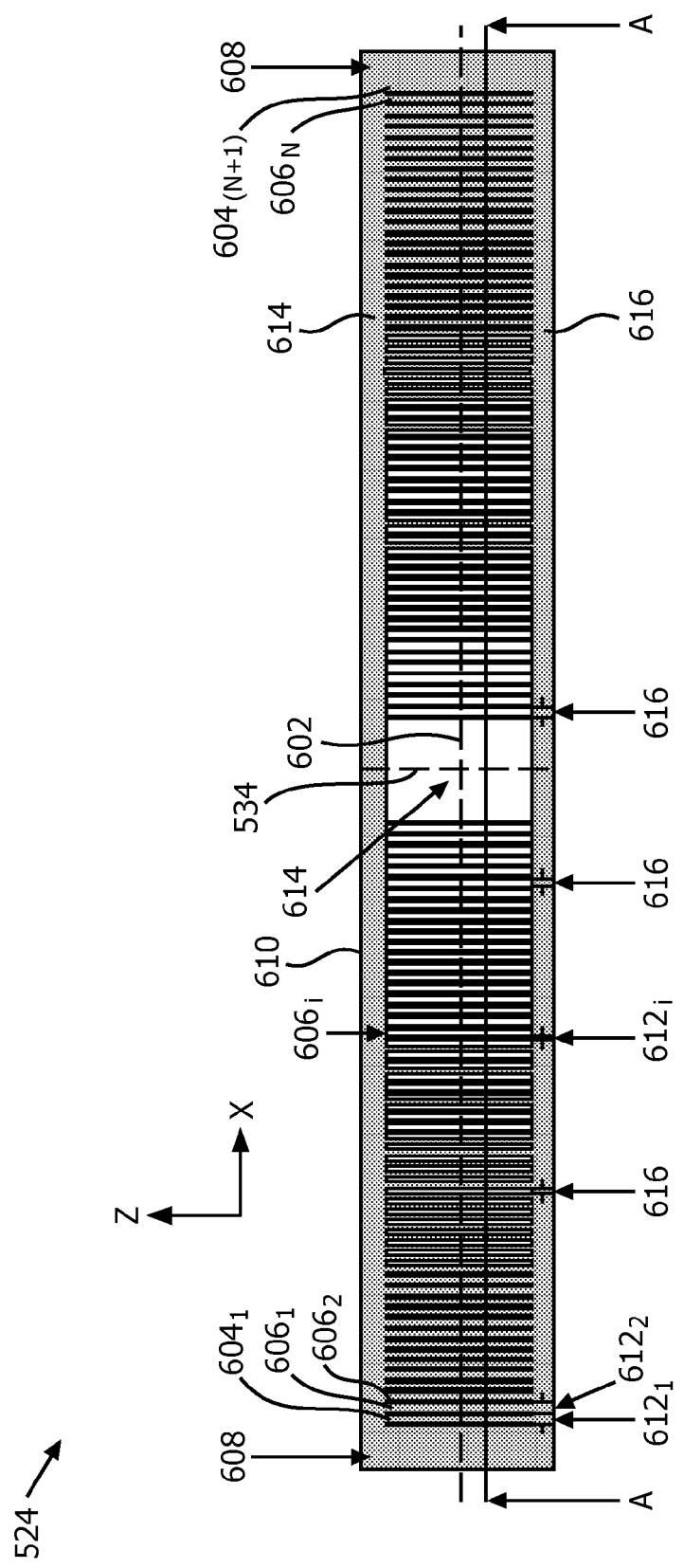

Turning to FIG. 6, a non-limiting example of the beam shaper 524, looking into the beam shaper 524 along a direction extending between the focal spot 510 and the collimator 512, is illustrated.

The illustrated beam shaper 524 is rectangular shaped having a longer axis 602 extending along a traverse or x direction and a shorter axis extending along the z-direction. In other embodiments, the beam shaper 524 can be otherwise shaped, e.g., one or more of the sides could be curved, irregular, etc. The beam shaper 524 includes a high-density, high-Z material such as tungsten, molybdenum or other suitable material. Generally, a suitable beam shaper attenuates more than 98% of the incident beam. The principal attenuation process of the high-Z material is the photoelectric effect, and, as such, the beam shaper 524 generates little to no scatter radiation. In addition, there is little to no beam hardening, because the transmitted beam goes through air.

The beam shaper 524 includes a plurality of elongate x-ray absorbing elements $606_1, 606_2, \ldots, 606_N$ (collectively referred to herein as x-ray absorbing elements 606), where N is an integer. The x-ray absorbing elements 606 are arranged parallel to each other along the longer axis 602. The x-ray absorbing elements 606 are respectively separated from a neighboring(s) x-ray absorbing element(s) 606 by a plurality of material free regions $604_1, \ldots, 604_{(N+1)}$ (collectively referred to herein as material free regions 604). End regions 608 of the elongate x-ray absorbing elements 606 are part of a support member 610 that encloses a perimeter of the beam shaper 524.

One or more of the x-ray absorbing elements 606 has a width that is greater than a width of one or more of the other x-ray absorbing elements 606. For example, a width $612_1$ of the x-ray absorbing elements $606_1$ is greater than a width $612_2$ of the x-ray absorbing elements $606_2$, which is greater than a width $612_i$ of an x-ray absorbing elements $606_i$. Generally, the widths sequentially decrease going from outer x-ray absorbing elements 606 to a central region 614. However, the widths do not have to sequentially change as such. In one instance, the slit widths decrease exponentially with the fan-angle.

In the illustrated embodiment, an element center to element center distance or a pitch 616 is the same for all of x-ray absorbing elements 606. In a variation, the pitch may vary at least with respect to one pair of x-ray absorbing elements 606. In a configuration with the same pitch 616 and widths 612 that sequentially decrease going outer x-ray absorbing element 606 to the central region 614, the material free regions 604 increase in width in the opposite direction, or from the central region to the outer regions.

Figure 7:
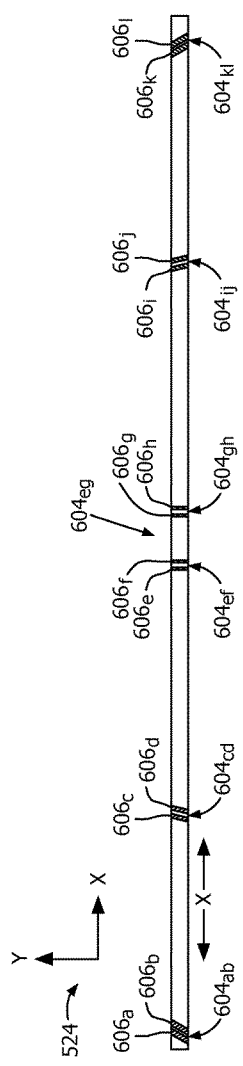

FIG. 7 illustrates a cross-sectional view along line A-A of FIG. 6 for a configuration in which the beam shaper 524 is flat (not curved) in the x-y plane.

For sake of brevity and clarity, a subset of x-ray absorbing elements 606, namely, x-ray absorbing elements $606_a$, $606_b$, $606_c$, $606_d$, $606_e$, $606_f$, $606_g$, $606_h$, $606_i$, $606_j$, $606_k$, and $606_l$, are shown. In this example, the x-ray absorbing elements 606 are focused at the focal spot 510 (FIG. 5) and thus angled with respect to the x-direction and each other. In a variation, the x-ray absorbing elements 606 are instead perpendicular to the x-axis and parallel to each other or otherwise unfocused with respect to the focal spot 510.

From at least the discussion of FIG. 5, the x-ray absorbing elements 606 vary in width, being wider nearer ends (e.g., x-ray absorbing elements $606_a$ and $606_l$) and narrower nearer a central region (e.g., x-ray absorbing elements $606_f$ and $606_g$). The individual x-ray absorbing elements 606 substantially block the radiation impingent thereon. The radiation traversing the material free regions 604 pass through the beam shaper 625 without blocking any of the radiation.

Figure 8:
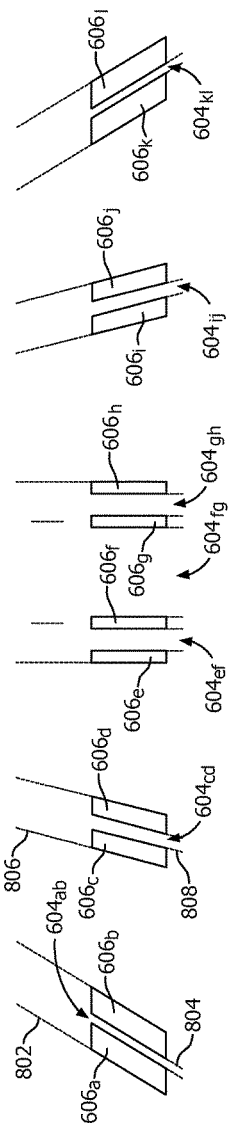

This is shown in FIG. 8. With respect to the x-ray absorbing elements $606_a$ and $606_b$, radiation 802 is impingent on the beam shaper 524, spanning across the x-ray absorbing element $606_a$, the material free region $604_{ab}$, and the x-ray absorbing element $606_b$. The radiation striking the x-ray absorbing elements $606_a$ and $606_b$ is blocked and the radiation traversing the material free region $604_{ab}$ passes through the material free region $604_{ab}$. As a result, radiation 804 passes through and exits the beam shaper 524. Note that more radiation is blocked than passes at this region.

With respect to the x-ray absorbing elements $606_c$ and $606_d$, radiation 806 is impingent on the beam shaper 524, spanning across the x-ray absorbing element $606_c$, the material free region $604_{cd}$, and the x-ray absorbing element $606_d$. The radiation striking the x-ray absorbing elements $606_c$ and $606_d$ is blocked and the radiation traversing the material free region $604_{cd}$ passes through the material free region $604_{cd}$. As a result, radiation 808 passes through and exits the beam shaper 524. Again, more radiation is blocked than passes at this region.

In FIG. 8, less radiation is blocked in connection with the x-ray absorbing elements $606_c$ and $606_d$, relative to the x-ray absorbing elements $606_a$ and $606_b$. With respect to the x-ray absorbing elements $606_e$ and $606_f$, more radiation passes through the material free region $604_{ef}$ than is blocked by the x-ray absorbing elements $606_e$ and $606_f$. With respect to the x-ray absorbing elements $606_f$ and $606_g$, substantially all of the radiation 806 spanning across the x-ray absorbing element $606_f$, the material free region $604_{fg}$, and the x-ray absorbing element $606_g$ passes through the beam shaper 524.

The intensity of the transmitted beam is a function of the radiation passing through the beam shaper 524 and thus the area of the material free regions 604. As such, the intensity of the beam with respect to the beam shaper 524 is greater nearer the central region. In one instance, with the illustrated configuration, the intensity at the central region is 100% and an intensity of the beam at the ends regions is between 0.0 to 1.0%.

The system 500 may include a plurality of different beam shapers 524 (e.g., large, medium, small, etc.) with different profiles for producing different intensity profiles, which can be alternately electronically moved into the path of the beam, for example, based on the physical characteristics of the subject and/or otherwise.

Moving to FIGS. 9 and 11, a cross-sectional view along line A-A of FIG. 6 for a configuration in which the beam shaper 524 includes multiple beam shapers, including sub-beam shapers $524_1$ and $524_2$ is illustrated.

The sub-beam shaper $524_1$ includes x-ray absorbing elements $606_{a1}$, $606_{b1}$, $606_{c1}$, $606_{d1}$, $606_{e1}$, $606_{f1}$, $606_{g1}$, $606_{h1}$, $606_{i1}$, $606_{j1}$, $606_{k1}$ and $606_{l1}$, and material free regions $604_{ab1}$, $604_{cd1}$, $604_{ef1}$, $604_{fg1}$, $604_{gh1}$, $604_{ij1}$, and $604_{kl1}$. The sub-beam shaper $524_2$ includes x-ray absorbing elements $606_{a2}$, $606_{b2}$, $606_{c2}$, $606_{d2}$, $606_{e2}$, $606_{f2}$, $606_{g2}$, $606_{h2}$, $606_{i2}$, $606_{j2}$, $606_{k2}$ and $606_{l2}$, and material free regions $604_{ab2}$, $604_{cd2}$, $604_{ef2}$, $604_{fg2}$, $604_{gh2}$, $604_{ij2}$, and $604_{kl2}$.

In FIG. 9, the x-ray absorbing elements 606 are aligned such that the same radiation that traverses the x-ray absorbing elements 606 of the sub-beam shaper $524_1$ traverses the sub-beam shaper $524_2$. This is shown in FIG. 10. In a variation, the x-ray absorbing elements 606 are not aligned as such. In FIG. 11, at least one of the sub-beam shapers $524_1$ or the sub-beam shaper $524_2$ has translated relative to the other of the at least one of the sub-beam shapers $524_1$ or the sub-beam shaper $524_2$ such that the x-ray absorbing elements 606 of the two sub-beam shapers $524_1$ and $524_2$ are no longer aligned. This is shown in FIG. 12. As a consequence, less radiation passes through the beam shaper 524.

Figure 13:
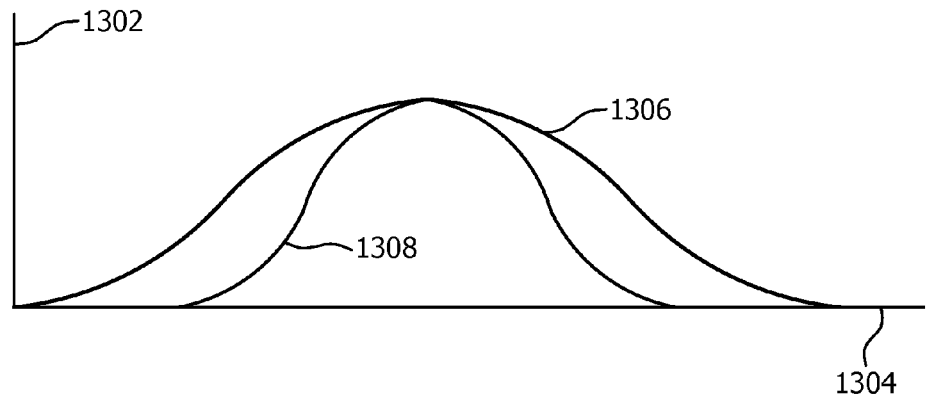

Again, the widths of the material free regions 604 decrease going from the central region to the end regions. As such, a given shift of a sub-beam shaper(s) results in a greater percentage decrease in intensity at the end regions. This is shown in FIG. 13 in which a y-axis 1302 represents intensity and an x-axis 1304 represents the x-ray absorbing element. A first profile 1306 shows the intensity profile for FIG. 9 in which the sub-beam shapers $524_1$ and $524_2$ are aligned, and a second profile 1308 shows the intensity profile for FIG. 11 in which the sub-beam shapers $524_1$ and $524_2$ are misaligned. Note that the intensity at the central region is about the same whereas the intensity at the peripheral regains falls off earlier in profile 1308.

The two illustrated positions of the sub-beam shapers $524_1$ and $524_2$ are not limiting and are provided for explanatory purposes. It is to be understood that other shifts between the sub-beam shapers $524_1$ and $524_2$ and/or more shifts between the sub-beam shapers $524_1$ and $524_2$ are also contemplated herein. The shifts may or may not be angular dependent such that the intensity profile of the beam can be dynamically changed as the focal spot 510 (FIG. 5) rotates about the examination region 506 around the subject in coordination with a physical profile of a non-cylindrical (e.g., an elliptical) shaped subject.

Figure 14:
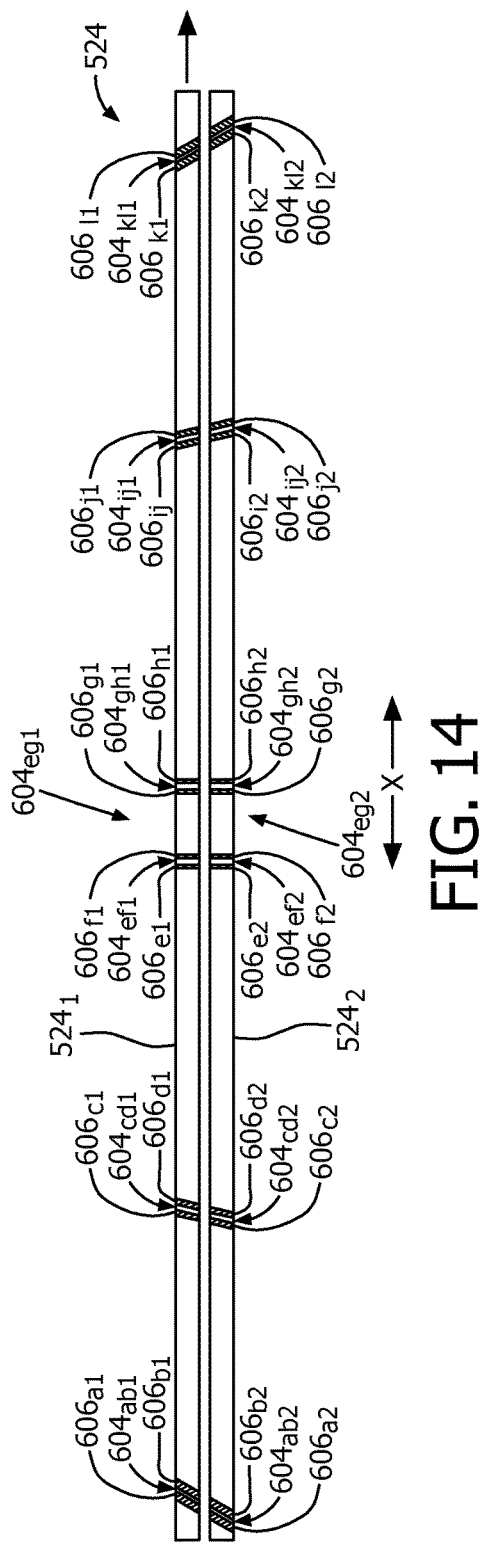
Figure 15:
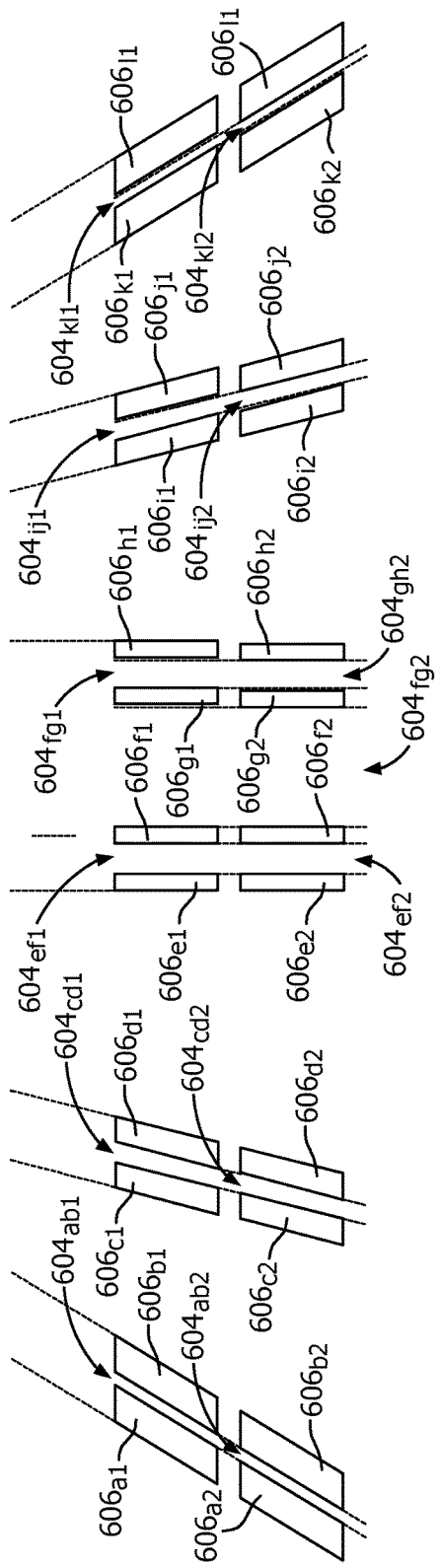

In FIG. 14, the sub-beam shaper $524_1$ includes a first partial sub-beam shaper $524_{1a}$ and a second partial sub-beam shaper $524_{1b}$. The first and second partial sub-beam shapers $524_{1a}$ and $524_{1b}$ can be independently controlled in that each of the first and second partial sub-beam shapers $524_{1a}$ and $524_{1b}$ can be translated independent of the other of the first and second partial sub-beam shapers $524_{1a}$ and $524_{1b}$. This includes translating both of the first and second partial sub-beam shapers $524_{1a}$ and $524_{1b}$ in the same direction or opposing directions, concurrently, or translating a single one of the first and second partial sub-beam shapers $524_{1a}$ and $524_{1b}$. The latter is shown in FIG. 15.

Likewise, the illustrated positions of the sub-beam shapers $524_{1a}$ and $524_{1b}$ are not limiting and are provided for explanatory purposes, and other shifts between the sub-beam shapers $524_{1a}$ and $524_{1b}$ and/or more shifts between the sub-beam shapers $524_{1a}$ and $524_{1b}$ are contemplated herein. Similarly, the shifts may or may not be dependent on the angular position of the gantry such that the intensity profile of the beam can be dynamically changed as the focal spot 510 (FIG. 5) rotates about the examination region 506 around the subject in coordination with a physical profile of a non-cylindrical (e.g., an elliptical) shaped subject.

Figure 16:
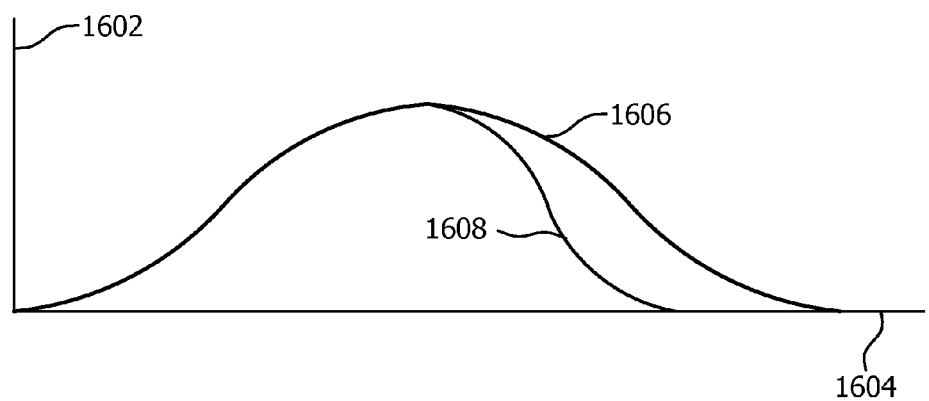

Furthermore, such shifts can be in coordination with a location of the subject, including an off-center subject, with respect to the iso-center 518 (FIG. 5). This is shown in FIG. 16 in which a y-axis 1602 represents intensity and an x-axis 1604 represents the x-ray absorbing element. A first profile 1606 shows the intensity profile for FIG. 14 in which the sub-beam shapers $524_1$ and $524_2$ are aligned, and a second profile 1608 shows the intensity profile for FIG. 14 in which one of the partial sub-beam shapers, the partial sub-beam shaper $524_{1b}$ in this example, independently shifts with respect to the sub-beam shaper $524_{1b}$, which remains at a static location.

With the configurations of FIGS. 9, 11 and 14, a sub-beam shaper can be translated based on the angle during a scan and/or translated prior to a scan and kept at a static position during the scan. With the former, the shifts can be applied for every angle or for only a sub-set of the angles. With the latter, a shift can be applied prior to scanning to adjust the beam shaper 524 based on a size (e.g., large, medium, small, etc.), location, and/or shape of the subject.

FIGS. 17, 18, and 19 show a variation in which the beam shaper 524 is curved, concave with respect to the focal spot 510 (FIG. 5). In this instance, the x-ray absorbing elements 606 are aligned parallel to each other and the beam shaper 524 is curved such that the individual x-ray absorbing elements 606 are focused at the focal spot 510 (FIG. 5). In another variation, at least one of the x-ray absorbing elements 606 is at least partially focused at the focal spot 510 (FIG. 5). FIGS. 11, 14 and 18 show that either sub-beam shaper 524 can be configured to translate and/or include multiple partial sub-beam shapers configured to translate.

With regard to FIGS. 5 and 6, actual values of the pitch 616, the widths of the material free regions 604, a length of the shaper and a number of x-ray absorbing elements 606 are based on one or more of a number of detectors in the detector array 522, a width of the detectors, a width of the detector array 522, a width of the beam, a source to shaper distance, a source to detector distance, a beam half angle, and a % modulation. Table 1 below shows one non-limiting approach to determine the pitch 616, the widths of the material free regions 604, and the number of x-ray absorbing elements 606.

TABLE 1

Beam Shaper Physical Characteristics.

| | |
|---|---|
| Pitch | $W_{det}$ |
| Material blocking region width | (% modulation)($W_{det}$) |
| Number of material free regions | ($N_{det}$) * ($W_{det}$) * ($sdd_1/sdd_2$)/$W_{source}$ |
| Width of shaper | cos(bha) * $sdd_1$ |

In Table 1, $W_{det}$ is a width of a detector, $N_{det}$ is a number of the detectors, $W_{source}$ is a width of the x-ray source, $sdd_1$ is a source to shaper distance, $sdd_2$ is a source to detector distance, and bha is beam half-angle, or the angle between a central ray and an end ray of the beam. The material free regions 604 can be formed by forming slits in a solid piece of suitable material via cutting with a saw, a laser, water, etc., and/or otherwise.

In a variation, the width of the x-ray absorbing elements 606 of the beam shaper 524 changes in the transverse or x direction as a function of the z direction as defined in FIG. 6. This can be achieved, for example, by making the material free regions 604 slightly thicker on one side of the beam shaper 524 relative to the other side of the beam shaper 524. This could be done in hardware and/or by tilting one with respect to the other. This may facilitate compensating for the heel-effect, which produces an intensity modulation in z, which has been compensated by a small wedge.

Figure 1:
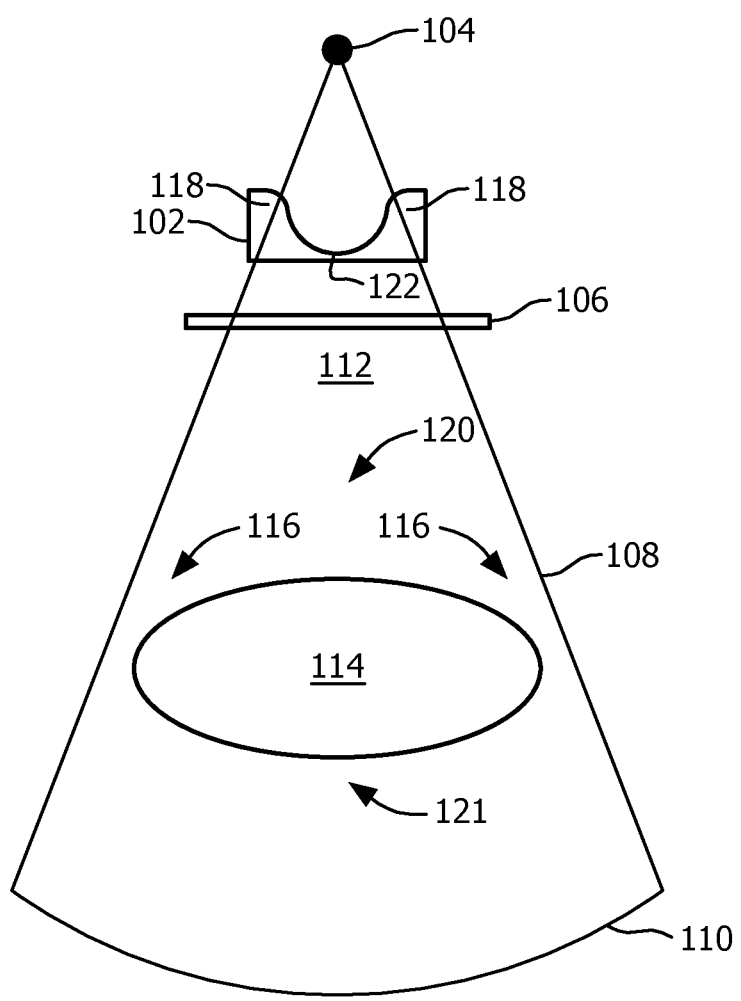
Figure 2:
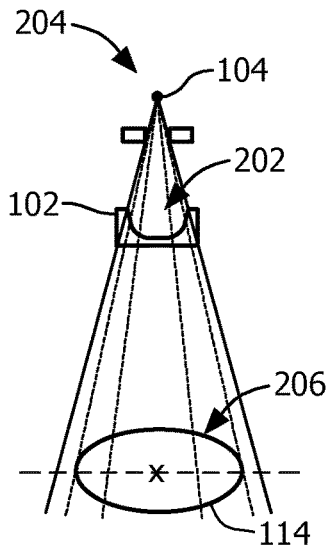
Figure 3:
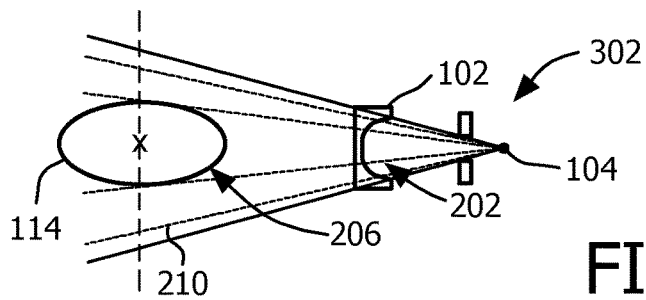
Figure 4:
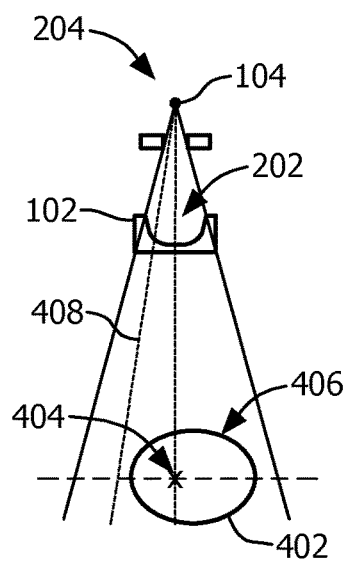

It is to be appreciated that the beam shaper 524 can be included in a scanner configuration that does not include a bowtie filter and that does include a bowtie filter, such as the bowtie filter discussed in connection with FIGS. 1, 2, 3, and/or 4.

Figure 20:
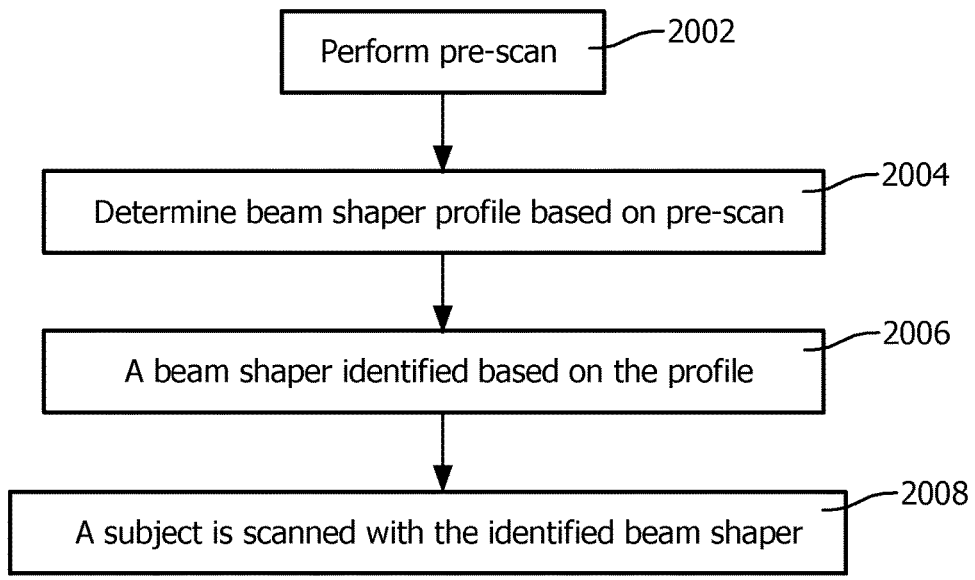
FIG. 20 illustrates a method for selecting a beam shaper.

FIG. 20 illustrates an example method in accordance with the embodiments described herein.

At 2002, a pre-scan of a subject or object is obtained. The pre-scan can be a 2D projection scan such as a scout scan, a 3D low volume scan, and/or other scan, such as a scan from a previous imaging examination.

At 2004, a beam shaper profile is determined based on the pre-scan. As described herein, this may include determining the profiled based on a shape of the subject and/or location of the subject with respect to iso-center.

At 2006, a beam shaper 524 is identified based on the profile and place in the path of the beam.

At 2008, the subject is scanned using the beam shaper.

Figure 21:
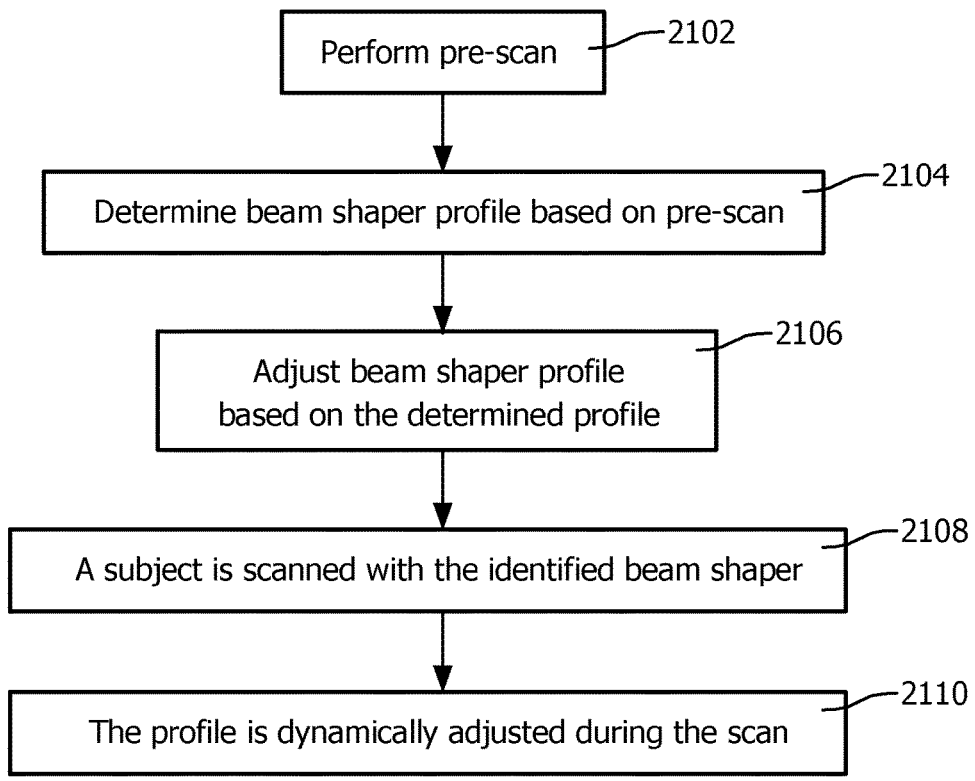
FIG. 21 illustrates a method adjusting a beam shaper.

FIG. 21 illustrates an example method in accordance with the embodiments described herein.

At 2102, a pre-scan of a subject or object is obtained. The pre-scan can be a 2D projection scan such as a scout scan, a 3D low volume scan, and/or other scan, such as a scan from a previous imaging examination.

At 2104, a beam shaper profile is determined based on the pre-scan. As described herein, this may include determining the profiled based on a shape of the subject and/or location of the subject with respect to iso-center.

At 2106, a profile of the beam shaper 524 is adjusted based on the profile.

At 2108, the subject is scanned.

At 2110, optionally the profile of the beam shaper 524 is dynamically adjusted during the scan.

It is to be appreciated that the ordering of the acts in the methods described herein is not limiting. As such, other orderings are contemplated herein. In addition, one or more acts may be omitted and/or one or more additional acts may be included.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a focal spot configured to rotate along a path around an examination region and emits radiation;
   a collimator configured to collimate the radiation, producing a radiation beam that traverses a field of view of the examination region;
   a detector array located opposite the radiation source, across the examination region, configured to detect radiation traversing the field of view and produces a signal indicative of the detected radiation; and
   a beam shaper, located between the radiation source and the collimator, configured to rotate in coordination with the focal spot and defines an intensity profile of the radiation beam,
   wherein the beam shaper includes a plurality of elongate x-ray absorbing elements arranged parallel to each other along a transverse direction with respect to a direction of the beam, separated from each other by a plurality of material free regions and widths of the plurality of x-ray absorbing elements along the transverse direction increase from a central region of the beam shaper towards end regions of the beam shaper, wherein each width of a corresponding elongate x-ray absorbing element of the plurality of elongate x-ray absorbing elements is uniform in the transverse direction and is defined by a distance along a line perpendicular to a direction from the focal spot to each of the elongate x-ray absorbing elements.

2. The imaging system of claim 1, wherein the widths of the plurality of x-ray absorbing elements increase exponentially with a fan-angle of the radiation beam.

3. The imaging system of claim 1, wherein a center to center distance of pairs of the plurality of x-ray absorbing elements is the same.

4. The imaging system of claim 1, wherein an intensity of the radiation exiting the beam shaper at the end regions of the beam shaper is less than one percent of the radiation impinging on the end regions of the beam shaper.

5. The imaging system of claim 1, wherein an intensity of the radiation exiting the beam shaper at the central region of the beam shaper is about equal to the radiation impinging on the central region of the beam shaper.

6. The imaging system of claim 1, the beam shaper, comprising:
   at least first and second sub-beam shapers arranged one on top of the other in the path of the radiation beam, wherein at least one of the first and second sub-beam shapers translates with respect to the other of the at least first and second sub-beam shapers.

7. The imaging system of claim 6, wherein translating at least one of the first and second sub-beam shapers with respect to the other of the at least first and second sub-beam shapers changes an output intensity of the beam shaper.

8. The imaging system of claim 7, wherein at least one of the first and second sub-beam shapers translates with respect to the other of the at least first and second sub-beam shapers during scanning, thereby changing the output intensity of the beam shaper as a function of acquisition angle.

9. The imaging system of claim 6, wherein the first or second sub-beam shapers that translates includes two partial beam shapers, wherein each of the partial beam shapers independently translates with respect to the other of the two partial beam shapers.

10. The imaging system of claim 9, wherein only one of the two partial beam shapers translates for a scan.

11. The imaging system of claim 1, wherein the x-ray absorbing elements are focused at the focal spot.

12. A method, comprising:
rotating a focal spot and a beam shaper in coordination on a path around an examination region,
wherein the beam shaper includes a plurality of elongate x-ray absorbing elements arranged parallel to each other along a transverse direction with respect to a direction of the beam, separated from each other by a plurality of material free regions, and defines an intensity profile of a radiation beam traversing the examination region and widths of the plurality of x-ray absorbing elements along the transverse direction increase from a central region of the beam shaper towards end regions of the beam shaper, wherein each width is defined by a distance along a line perpendicular to a direction from the focal spot to each of the elongate x-ray absorbing elements, wherein each width of a corresponding elongate x-ray absorbing element of the plurality of elongate x-ray absorbing elements is uniform along a length of the corresponding elongate x-ray absorbing element in the direction of the beam; and
detecting radiation emitted by the focal spot that traverses the beam shaper and the examination region a field of view, and illuminates a detector array located opposite the focal spot, and generating an output signal indicative thereof.

13. The method of claim 12, wherein a center to center distance of pairs of the plurality of x-ray absorbing elements is the same.

14. The method of claim 12, wherein the beam shaper includes at least first and second sub-beam shapers arranged one on top of the other in the path of the radiation beam and at least one of the first or second sub-beam shapers is configured to translate with respect to the other of the at least first and second sub-beam shapers, and further comprising:
translating the at least one of the first or second sub-beam shapers with respect to the other of the at least first and second sub-beam shapers prior to scanning a subject.

15. The method of claim 14, further comprising:
translating the at least one of the first or second sub-beam shapers with respect to the other of the at least first and second sub-beam shapers prior to or while scanning the subject.

16. The method of claim 15, wherein translating the at least one of the first or second sub-beam shapers with respect to the other of the at least first and second sub-beam shapers prior to or while scanning the subject changes the intensity profile of the radiation beam while scanning the subject.

17. A beam shaper of an imaging system, comprising:
a plurality of elongate x-ray absorbing elements arranged parallel to each other along a transverse direction with respect to a direction of the beam, separated from each other by a plurality of material free regions, and widths of the plurality of x-ray absorbing elements in the transverse direction increase from a central region of the beam shaper towards end regions of the beam shaper, wherein each width is defined by a distance along a line perpendicular to a direction from the focal spot to each of the elongate x-ray absorbing elements, wherein a first elongate x-ray absorbing element of the plurality of elongate x-ray absorbing elements includes a first width and is located in the central region and a second elongate x-ray absorbing element of the plurality of elongate x-ray absorbing elements includes a second width and is located in one of the end regions and the second width is greater than the first width.

18. The beam shaper of claim 17, wherein a center to center distance of pairs of the plurality of x-ray absorbing elements is the same.

19. The beam shaper of claim 18, wherein the widths increase as a function of a z-direction.

20. The beam shaper of claim 17, wherein the beam shaper is flat in an x-y plane.

21. The beam shaper of claim 17, wherein the beam shaper is curved in an x-y plane.

* * * * *